US00PP09782P

United States Patent [19]

Frazer

[11] Patent Number: Plant 9,782

[45] Date of Patent: Jan. 14, 1997

[54] DIEFFENBACHIA PLANT NAMED 'TROPIC BREEZE'

[75] Inventor: Edwin J. Frazer, Kenmore, Australia

[73] Assignee: Twyford International Inc., Santa Paula, Calif.

[21] Appl. No.: 422,899

[22] Filed: Apr. 17, 1995

[51] Int. Cl.[6] ..... A01H 5/00

[52] U.S. Cl. ..... Plt./88.2

[58] Field of Search ..... Plt./88.2

*Primary Examiner*—James R. Feyrer
*Attorney, Agent, or Firm*—Foley & Lardner

[57] ABSTRACT

A dieffenbachia plant named Tropic Breeze characterized by its long narrow elliptical leaves abundantly marked with yellow-green, white, and dark green visible from both sides of the leaf. The colors darken as the leaf ages. The habit is branched, rosetted and distinctly upright. These combined characteristics make Tropic Breeze a unique new cultivar.

3 Drawing Sheets

The present invention comprises a new and distinct cultivar of Dieffenbachia, botanically known as *Dieffenbachia hybrida*, and referred to by the cultivar name Tropic Breeze.

The new cultivar is a product of a planned breeding program carried out by the inventor Edwin J. Frazer in Brisbane, Australia. The new cultivar is a product of a cross made by the inventor between presently unidentified parents of the following species:

Pollen parent: *Dieffenbachia picta angustior lancifolia.*
Seed parent: *Dieffenbachia fourneri.*

The cultivar was discovered from the progeny of the stated cross by Edwin J. Frazer. Asexual propagation by tissue culture by the inventor in Brisbane, Australia increased the number of plants for evaluation and has demonstrated the stability of the combination of characteristics of Tropic Breeze from generation to generation.

The following observations, measurements and values describe plants grown in Apopka, Fla. under greenhouse conditions which closely approximate those generally used in horticultural practice.

The following traits have been repeatedly observed to be characteristics which in combination particularly distinguish Tropic Breeze from other cultivars.

1. The leaves are long, narrow, elliptic, and distinctly tapered at the tip and base.
2. The leaves are abundantly marked with yellow-green, white and dark green.
3. The color pattern is visible from both sides of the leaf.
4. The youngest leaves are colorful, having more white and yellow-green markings than the oldest leaves.
5. The growth habit is branched, and the leaves are rosetted and held upright.

All color references are measured against The Royal Horticultural Society Colour Chart. Colors are approximate as color depends on horticultural practices such as light level and fertilization rate, among others, without, however, any variance in genotype.

The color photographic drawing comprising Sheet 1 is a top perspective view of a plant of Tropic Breeze in a 21 cm pot approximately 40 weeks after planting a 12 week old liner obtained by tissue culture and grown under appropriate growing conditions.

The color photocopies comprising Sheets 2 and 3 illustrate the detail of the color pattern, and differences in color between newly expanded (Sheet 2) and mature leaves (Sheet 3).

In both of Sheets 2 and 3 the top surface of the leaves are shown on the left, and the bottom surfaces on the right.

Colors are as accurate as possible with color illustrations of this type.

Origin: Sterile seedling selected from a cross of presently unknown parents.

*Pollen parent.*—*Dieffenbachia picta angustior lancifolia.*

*Seed parent.*—*Dieffenbachia fourneri.*

Classification: *Dieffenbachia hybrida*, cv, Tropic Breeze.

Propagation: Asexual propagation either by tissue culture or division.

Plant: In a 21 cm pot for a plant grown from a 12 week old liner after 40 weeks under appropriate growing conditions, Tropic Breeze has a height of approximately 24 cm to 27.5 cm from the soil surface to the junction of the petioles of the last two (2) unrolled leaves, and a width of approximately 59 to 63 cm.

*Stem.*—Growth pattern: The stem is erect in growth and approximately 2.9 cm in diameter five (5) cm above the soil surface. Internode distance is approximately 1.1 cm to 1.3 cm three (3) cm above the soil. Color: The stem is 147A–B.

*Petiole.*—The following information is based on the 4th expanded leaf from the apex. Growth pattern: The petiole has fleshy edges, referred to as wings, extending from the midrib. The wings are approximately 7 mm to 12 mm wide one-half (½) the distance from the petiole base to the wing apex. The wings extend from the base of the petiole to within approximately 0.7 cm to 1.0 cm of the base of the leaf. The apex of the wings is unevenly emarginate. The petiole follows the stem axis but diverges from the axis approximately 11.7 cm to 9.8 cm from the leaf base, forming a horizontal distance from the edge of the stem to the leaf base of the approximately 2.5 cm. Dimensions: The petiole is straight from its base to the base of the leaf. The petiole is approximately 5 mm to 7 mm in diameter one-half (½) the distance between the top of the wing and the base of the leaf. The petiole is approximately 16 cm in length from its base to the base of the leaf. Color: The petiole wings are 137A, coarsely mottled and streaked with 137C and 145C. The base of the petiole at the point of attachment to the stem is 155A. The midrib of the petiole is darker than, but closest to, 137A.

Leaf:

*Growth pattern.*—The leaf is narrow and elliptical with an acuminate apex and an attenuate to acute cuneate base. The margin is entire. The leaf is asymmetric, with the side of the leaf unrolling first having less surface area than the side unrolling last. The leaf is oriented parallel to the stem axis at the time of full unrolling, changing to approximately 50 degrees from the stem axis as more leaves unroll above it. The midrib is straight over the length of the leaf. The leaf blade is convex between the primary veins.

*Dimensions.*—For the pot size and growing time indicated, the largest leaf is approximately 32 cm to 34.5 cm long and approximately 10.2 cm to 11.5 cm wide. An average sized leaf is approximately 27.7 cm to 29.5 cm long and approximately 8 cm to 9.5 cm wide. The leaf is moderately thick, and the surface is glossy.

*Midrib.*—The midrib is thick and prominent.

*Primary veins.*—The primary veins are sunken into the upper surface and protrude from the underside. The primary veins are the same color as the surrounding tissue.

*Pattern.*—The upper surface of both the mature leaf and the newly opened leaf is variously marked with large areas of yellow green, white and green, which areas darken with age.

*Color.*—Mature leaf upper surface: 145A–C, with spots and streaks darker and greener than, but closest to 137A. The margin is darker and greener than, but closest to 137A. Midrib is 155A, with streaks of 146A. Lower surface: 145B, 146D with spots and streaks of 137B. Midrib is 146D. Newly opened leaf upper surface: 4D with blotches of 150C and 137A. The leaf margin is 137A. Midrib is 155A, with streaks of 146C–D. Lower surface: 4D with blotches of 150C–D and 137B. The leaf margin is 137B. Midrib is darker than, but closest to 145D, with streaks greener than, but closest to 146B–C.

*Axillary breaks.*—There are approximately 3 to 5 axillary breaks with at least one leaf expanded. Leaves show color by the second leaf and have true color and pattern by the third leaf.

*Inflorescence.*—Typical of Dieffenbachia and does not have commercial significance.

Roots: Thick white roots with fine laterals.

It is claimed:

1. A new and distinct cultivar of Dieffenbachia plant named Tropic Breeze, as illustrated and described.

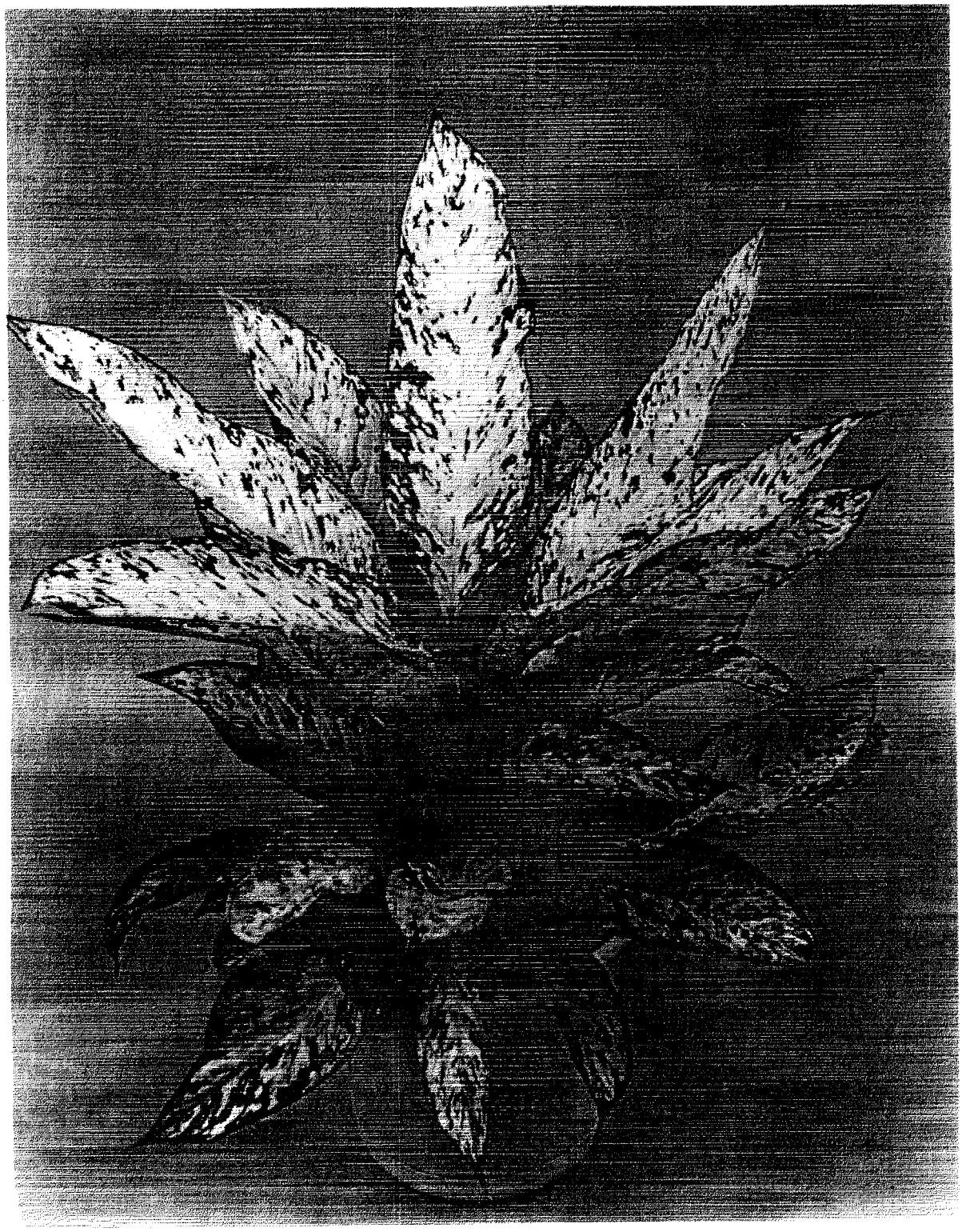

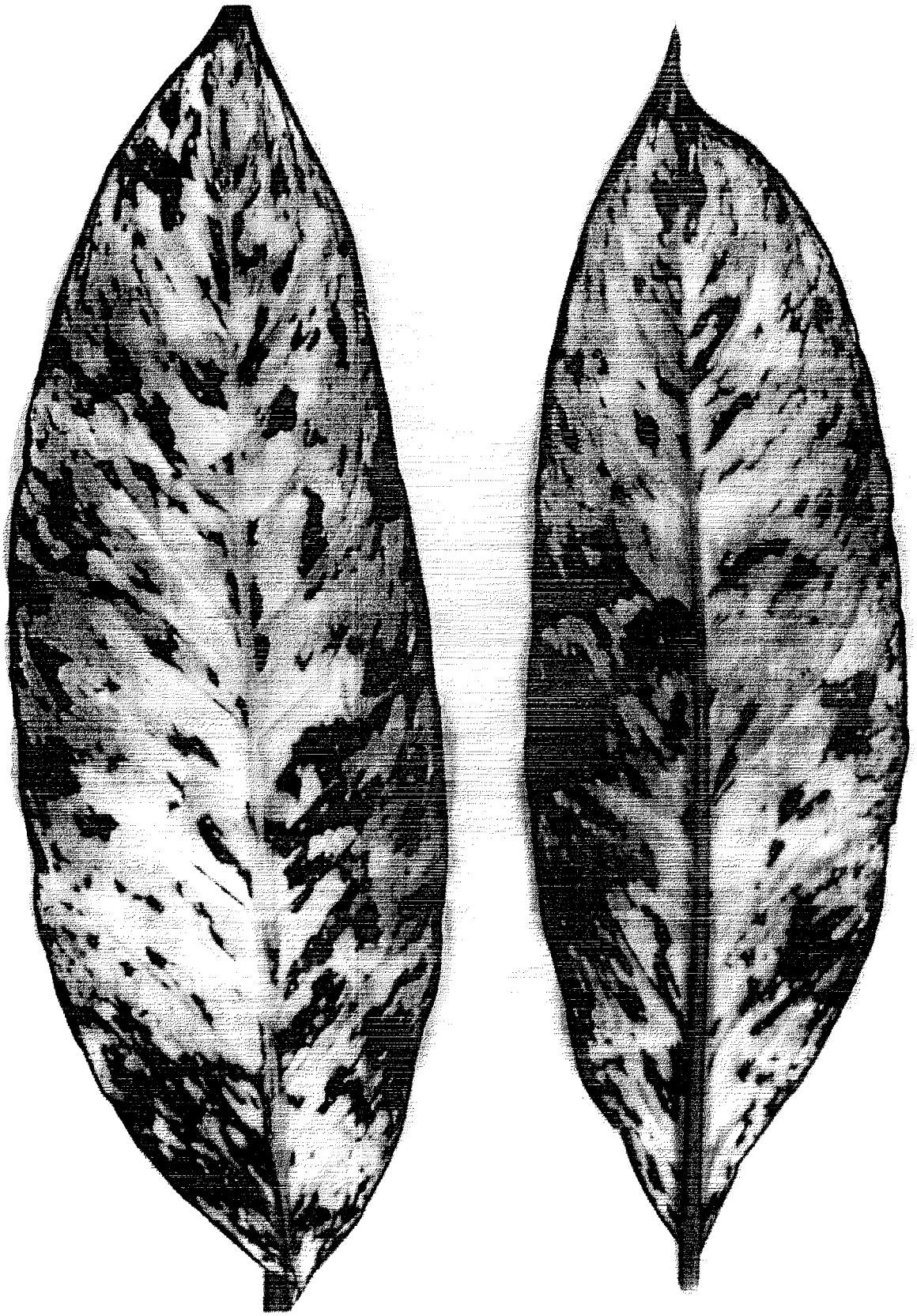

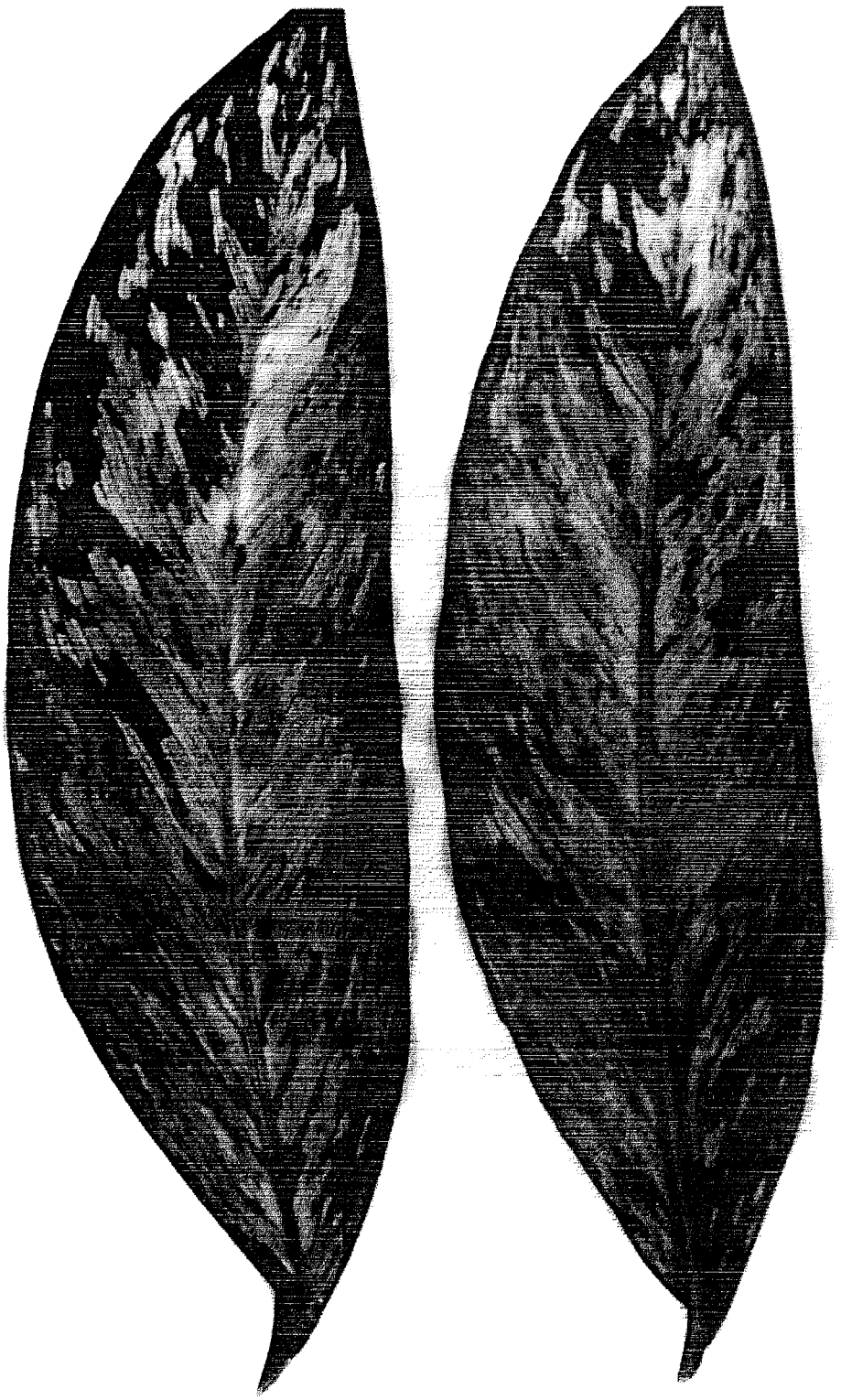

* * * * *